United States Patent
Alavi

(10) Patent No.: US 9,957,380 B2
(45) Date of Patent: May 1, 2018

(54) FORMALDEHYDE-FREE SMOKE REDUCTION AGENTS FOR BINDERS

(71) Applicant: JOHNS MANVILLE, Denver, CO (US)

(72) Inventor: Kiarash Alavi, Littleton, CO (US)

(73) Assignee: Johns Manville, Denver, CO (US)

( * ) Notice: Subject to any disclaimer, the term of this patent is extended or adjusted under 35 U.S.C. 154(b) by 34 days.

(21) Appl. No.: 14/689,102

(22) Filed: Apr. 17, 2015

(65) Prior Publication Data

US 2016/0304705 A1   Oct. 20, 2016

(51) Int. Cl.
| C08L 1/00 | (2006.01) |
| B32B 17/00 | (2006.01) |
| C08L 5/00 | (2006.01) |

(52) U.S. Cl.
CPC ..................................... C08L 5/00 (2013.01)

(58) Field of Classification Search
None
See application file for complete search history.

(56) References Cited

U.S. PATENT DOCUMENTS

| | | | |
|---|---|---|---|
| 4,472,167 A * | 9/1984 | Welch ................. | D06M 13/148 8/116.4 |
| 7,854,980 B2 | 12/2010 | Jackson et al. | |
| 8,377,564 B2 | 2/2013 | Shooshtari et al. | |
| 2006/0111480 A1 * | 5/2006 | Hansen ................. | C03C 25/246 524/27 |
| 2010/0330376 A1 * | 12/2010 | Trksak .................... | C08B 11/08 428/426 |
| 2011/0039111 A1 | 2/2011 | Shooshtari | |
| 2012/0064414 A1 * | 3/2012 | Leitner ................ | B01D 15/361 429/331 |
| 2012/0093742 A1 * | 4/2012 | Kaouas ............... | A23L 1/22671 424/49 |
| 2013/0283688 A1 * | 10/2013 | Naerum ............... | A01G 31/001 47/59 S |
| 2013/0327250 A1 * | 12/2013 | Shooshtari ................ | C08L 1/00 106/217.5 |
| 2014/0134497 A1 * | 5/2014 | Lester .................... | D21H 23/48 429/249 |
| 2014/0134909 A1 | 5/2014 | Guo et al. | |
| 2014/0308453 A1 * | 10/2014 | Shooshtari .......... | D06M 13/165 427/394 |
| 2014/0322477 A1 * | 10/2014 | Jeon ......................... | F24B 1/24 428/76 |

* cited by examiner

Primary Examiner — Melvin C Mayes
Assistant Examiner — Colette Nguyen
(74) Attorney, Agent, or Firm — Robert D. Touslee

(57) ABSTRACT

Embodiments of the present technology may include a curable, carbohydrate binder composition. The composition may include a carbohydrate. The composition may also include a urea compound. The composition may further include a nitrogen-containing compound. The nitrogen-containing compound may not be the urea compound.

20 Claims, 2 Drawing Sheets

FORMALDEHYDE-FREE SMOKE REDUCTION AGENTS FOR BINDERS

BACKGROUND

For decades, urea formaldehyde (UF), phenol formaldehyde (PF), and melamine formaldehyde (MF) binder compositions have been used to make glass fiber mats for building materials, including insulation, flooring, siding, facers, and roofing shingles. Formaldehyde binders were favored for these materials because of their low cost and acceptable strength properties. For materials like roofing shingles, the UF, PF, or MF in the binder compositions were often blended with more flexible latex polymers such as polyvinyl acetate, vinyl acrylic, and/or styrene butadiene polymers. The latexes in the binders gave the shingles increased tensile and tear strength, as well as improved their moisture resistance properties.

More recently, the construction industry has moved away from formaldehyde-based binder compositions. Formaldehyde is considered a probable human carcinogen, as well as an irritant and an allergen, and its use in binder formulations for building products, textiles, upholstery, and other materials is increasingly restricted. Thus, makers of building materials have been developing alternative binder formulations that are formaldehyde free.

One alternative binder system that has received considerable attention includes the polymerization of carbohydrates (i.e., sugars) with amine compounds to make a binder that is insoluble in water and adheres well to glass fibers. In addition to being formaldehyde-free, these carbohydrate-based binder formulations can be made from renewably grown natural sugars instead of non-renewable, petroleum-based feedstocks.

Producing formaldehyde-free fiber composites may result in byproducts, which may reduce the energy and/or economic efficiency of the process. Thus, there is a need for alternative compositions and methods to produce formaldehyde-free fiber composites.

BRIEF SUMMARY

Embodiments of the present technology may produce binder compositions, that when raised to a curing temperature, emit fewer volatile organic compounds (VOCs) than conventional binder compositions. VOCs may result from acid or heat degradation products of carbohydrates. The VOCs may include aldehyde or ketone moieties. Lower VOC binder compositions may include a urea. While the urea may not play a significant role in the binder properties of the binder composition, the urea may bond to the aldehyde and ketone moieties in the carbohydrate degradation products. The reaction of the urea with the aldehyde and ketone moieties may reduce the volatility of the compounds and as a result, may decrease VOC emissions. Binder compositions may reduce, suppress, and/or prevent smoke from the binder compositions.

Embodiments of the present technology may include a curable, carbohydrate binder composition. The composition may include a carbohydrate. The composition may also include a urea. The composition may further include a nitrogen-containing compound. The nitrogen-containing compound may not be the urea.

Embodiments of the present technology may also include a method of reducing volatile organic compound emission during curing of a carbohydrate binder composition. The method may include forming an aqueous dispersion of fibers. The method may further include applying a binder composition to the aqueous dispersion of fibers to form a binder-fiber mixture. The binder composition may include a carbohydrate, a urea compound, and a nitrogen-containing compound that is not the urea compound. Additionally, the method may include curing the binder-fiber mixture to form a fiber-containing composite.

Embodiments of the present technology may include a fiber-containing composite. The fiber-containing composite may include glass fibers. The fiber-containing composite may also include a binder. The binder may include cured products from a carbohydrate binder composition. The carbohydrate binder composition may include a carbohydrate, a urea compound, and a nitrogen-containing compound that is not the urea compound. The fiber-containing composite may further include a reaction product of the urea compound and an aldehyde or a ketone from a degradation product of the carbohydrate.

DETAILED DESCRIPTION

Figure 1:
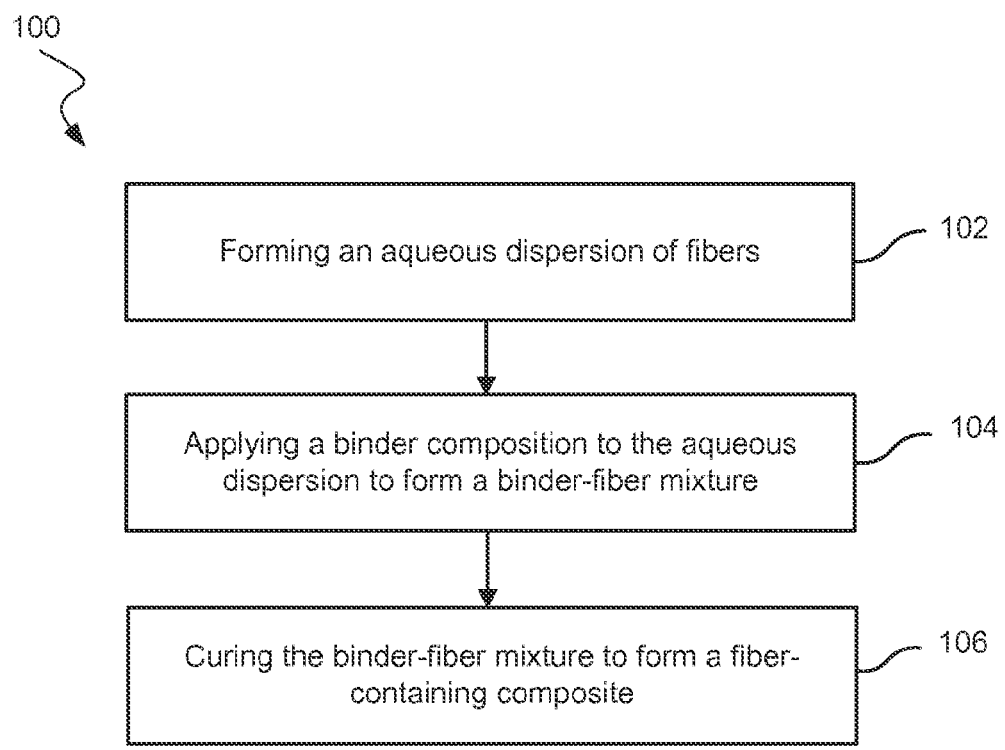
FIG. 1 shows a simplified block flow diagram of a method of reducing emissions according to embodiments of the present technology.

Conventional carbohydrate binder compositions may include carbohydrate degradation products, other binder component degradation products, and other compounds, which upon curing the composition may produce smoke and/or emit volatile organic compounds (VOCs). Abating the emissions, rather than reducing, suppressing, or preventing the emissions, is often the conventional method in addressing VOC emissions and smoke production. Abatement methods include burning, scrubbing, or filtering the VOCs. However, these abatement methods may require additional or larger unit operations, create additional waste streams, decrease energy efficiency, and/or decrease economic efficiency.

Embodiments of the present technology may eliminate or reduce the need to abate emissions. Instead, embodiments of the present technology may reduce, suppress, and/or prevent VOC emissions. Without intending to be bound by any particular theory, it is believed that a urea compound may react with compounds that would otherwise volatilize under cure temperatures. Solid particles may precipitate onto the VOCs and form smoke. The reaction between the urea compound and the otherwise volatile compounds may result in a compound with lower volatility. These reaction products may become incorporated in a cured binder.

Embodiments of the present technology may include a curable, carbohydrate binder composition. The binder composition may be substantially or completely free of formaldehyde. Substantially free may mean that the binder composition does not have an amount of formaldehyde that would affect the binder properties of the composition. For example, the binder composition may have trace amounts of formaldehyde.

The composition may include a carbohydrate. The carbohydrate may include a reducing sugar. Carbohydrates are described in greater detail later in the specification, and the composition may include any carbohydrate described.

The composition may also include a nitrogen-containing compound. The nitrogen-containing compound may not include a urea compound. However, the nitrogen-containing compound may include the reaction product of a urea compound with a glyoxal. The urea compound and the glyoxal may react with equimolar amounts. The nitrogen-containing compound may include 4,5-dihydroxyimidazolidin-2-one, an amino-amic acid, an inorganic salt of a diamine or a polyamine, or an ammonium salt of a carboxylic acid. Nitrogen-containing compounds are described later in this specification, and the composition may include or exclude any nitrogen-containing compound or any groups of nitrogen-containing compounds described.

The composition may further include a urea compound. The molar ratio of the urea compound to the nitrogen-containing compound may be 0.1 or greater, 0.5 or greater, 1 or greater, 1.5 or greater, or 2 or greater in embodiments. The molar ratio of the urea to the binder may be 0.1 or greater, 0.5 or greater, 1 or greater, 1.5 or greater, or 2 or greater in embodiments.

More specifically, the urea compound may be a substituted or unsubstituted urea having the formula:

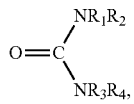

where $R_1$, $R_2$, $R_3$, and $R_4$ are independently chosen from a hydrogen moiety (H), an alkyl group, an aromatic group, an alcohol group, an aldehyde group, a ketone group, a carboxylic acid group, and an alkoxy group. Exemplary alkyl groups include straight-chained, branched, or cyclic hydrocarbons of varying size (e.g., $C_1$-$C_{12}$, $C_1$-$C_8$, $C_1$-$C_4$, etc.). Exemplary aromatic (i.e., aryl) groups include substituted or unsubstituted phenyl moieties, among other aromatic constituents. Exemplary alcohol groups include —ROH, where R may be a substituted or unsubstituted, saturated or unsaturated, branched or unbranched, cyclic or acyclic, organic moiety. For example, R may be —$(CH_2)_n$—, where n may be 1 to 12. Exemplary alcohols may also include polyols having two or more hydroxyl groups (—OH) in alcohol group. Exemplary aldehyde groups include —RC(=O)H, where R may be a monovalent functional group (e.g., a single bond), or a substituted or unsubstituted, saturated or unsaturated, branched or unbranched, cyclic or acyclic, organic moiety, such as —$(CH_2)_n$—, where n may be 1 to 12. Exemplary ketone groups may include —RC(=O)R' where R and R' can be variety of carbon containing constituents. Exemplary carboxylic acid groups may include —R—COOH, where R may be a monovalent functional group, such as a single bond, or a variety of carbon-containing constituents. Exemplary alkoxy groups include —$OR_x$, where $R_x$ is an alkyl group. The reaction product of a urea compound and a glyoxal may not be defined as a urea compound.

The composition may further include an acid. The acid may improve the kinetics of a reaction between the carbohydrate and the nitrogen-containing compound. The acid may not have an effect on the VOC emissions. The acid may include a carboxylic acid. The carboxylic acid may include a monocarboxylic acid, an aromatic carboxylic acid, a dicarboxylic acid, or a tricarboxylic acid. The carboxylic acid may include citric acid. Citric acid may be present in an amount of 0.5 mole per 1 mole of the urea. Citric acid may be present in an amount between about 0.1 mole and about 2 moles, about 0.1 mole and about 0.5 mole, about 0.5 mole and about 1 mole, about 1 mole and about 1.5 moles, about 1.5 moles and about 2 moles of the urea in embodiments. The pH of the resin before adding acid may be between about 5 and about 8, between about 5 and about 6, between about 6 and about 7, or between about 7 and about 8 according to embodiments. After adding the acid, the pH of the resin may be between about 2 and about 5, between about 2 and about 3, between about 3 and about 4, or between about 4 and about 5 according to embodiments. The composition may further include an adhesion promoter, a filler, a catalyst, a wax, or a release agent.

The composition, when cured, may emit fewer volatile organic compounds than the composition without the urea compound. The composition may be cured at a temperature from about 100° C. to about 300° C., from about 100° C. to about 200° C., from about 200° C. to about 300° C., from about 180° C. to about 220° C., or from about 150° C. to about 250° C. in embodiments. The composition when cured may emit 50% or less of the VOCs emitted by mass when a composition without the urea compound is cured. In other words, using the composition may result in a reduction in VOCs emitted of 50% or more. Additionally, the composition when cured may emit 10% or less of the VOCs emitted when a composition without the urea compound is cured. Using the composition may result in a reduction in VOCs emitted of 90% or more. The mechanical strength of the cured binder composition may be the same or better than the mechanical strength of the cured binder composition without the urea compound. The composition may emit 60% or less, 40% or less, 30% or less, or 20% or less of the VOCs emitted when a composition without the urea compound is cured.

As shown in FIG. 1, embodiments of the present technology may also include a method 100 of reducing volatile organic compound emission during curing of a carbohydrate binder composition. Method 100 may include forming an aqueous dispersion of fibers 102. In some embodiments, method 100 may also include passing the aqueous dispersion through a mat forming screen to form a wet mat. Method 100 may further include applying a binder composition to the aqueous dispersion of fibers to form a binder-fiber mixture 104.

The binder composition may include a carbohydrate, a nitrogen-containing compound that is not a urea compound, and a urea compound. The binder composition may be any binder composition described herein.

Additionally, method 100 may include curing the binder-containing wet mat to form a fiber-containing composite 106. Curing the binder-containing wet mat may be at any temperature described herein. Curing the binder composition may emit fewer VOCs than curing a binder-fiber mixture with a binder of the same composition except for the urea. Curing the binder-fiber mixture may produce zero opacity smoke. In other embodiments, curing the binder-fiber mixture may produce smoke with 60% or less opacity, 70% or less opacity, 80% or less opacity, or 90% or less opacity of the smoke produced from a binder of the same composition except for the urea.

The fiber-containing composite may also include a binder. The binder may include cured products from a carbohydrate binder composition. The carbohydrate binder composition may include a carbohydrate, a urea compound, and a nitrogen-containing compound that is not the urea compound. The carbohydrate binder composition may be any carbohydrate binder composition described herein.

The fiber-containing composite may further include a reaction product of the urea compound and an aldehyde or a ketone from a degradation product of the carbohydrate.

The reaction product may not be volatile at a temperature from about 100° C. to about 300° C. or at any of the curing temperatures described herein.

The fiber-containing composites may take a variety of forms, for example construction materials including piping insulation, duct boards (e.g., air duct boards), and building insulation, reinforcement scrim, and roofing membranes, among other construction materials. Additional examples may include loose-fill blown insulation, duct liner, duct wrap, flexible duct media, pipe insulation, tank insulation, rigid plenum liner, textile duct liner insulation, equipment liner, oven insulation, elevated temperature board, elevated temperature wrap, elevated temperature panel, insulation batts and rolls, heavy density batt insulation, light density batt insulation, exterior foundation insulation board, and marine hull insulation, among other materials. The composites can also find use in printed circuit boards, battery separators, and filter stock, among other applications.

Figure 2A:
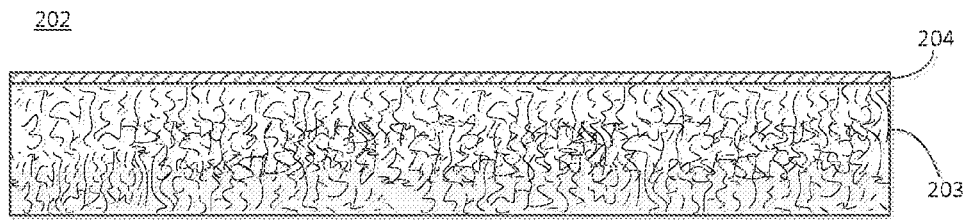
FIGS. 2A-C show simplified illustrations of exemplary composite materials according to embodiments.
Figure 2B:
Figure 2C:
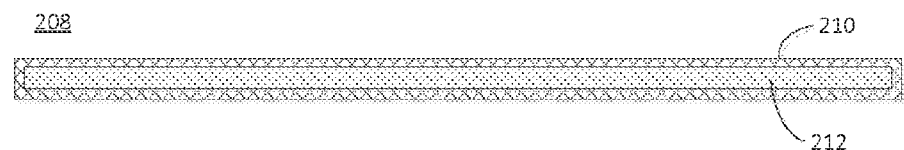

FIGS. 2A-C illustrate some of these exemplary composite materials. FIG. 2A is a simplified schematic of an exemplary fiber-containing batt material 202 that may be used for building insulation. The material 202 may include a batt 203 of non-woven fibers held together by the binder. The fibers may be glass fibers used to make fiberglass insulation (e.g, low-density or high-density fiberglass insulation), or a blend of two or more types of fibers, such as a blend of glass fibers and organic polymer fibers, among other types of fibers. In some examples, a facer 204 may be attached to one or more surfaces of the batt 203.

FIG. 2B is a simplified schematic of an exemplary fiber-containing composite board 206 that may be used as an insulation board, duct board, elevated temperature board, etc. The fibers in board 206 may include glass fibers, organic polymer fibers, inorganic fibers, carbon fibers, mineral fibers, metal fibers, among other types of fibers, and blends of two or more types of fibers.

FIG. 2C is a simplified schematic of an exemplary fiber-containing flexible insulation material 208 that may be used as a wrap and/or liner for ducts, pipes, tanks, equipment, etc. The fiber-containing flexible insulation material 208 may include a facer 210 attached to one or more surfaces of the fiber material 212. Exemplary materials for the facer 210 may include fire-resistant foil-scrim-kraft facing.

Specific examples of fiber-containing composites that use the present binder compositions include low-density fiberglass insulation (e.g., less than about 0.5 lbs/ft$^3$) and high-density fiberglass insulation.

The present binder compositions may be used in methods of binding fibers to make the fiber-containing composites. The fiber-containing composites may include fibers of one or more types, such as glass fibers, carbon fibers, and organic polymer fibers, among other types of fibers. The binder compositions used to make the composites may include a reducing sugar and a reaction product of a urea compound and an aldehyde-containing compound as described herein. The methods may include the step of applying the binder composition to a mat of woven or non-woven fibers to make a curable binder-fiber amalgam. The curable amalgam is then cured to form the fiber-containing composite of fibers bound together by the cured binder.

The step of applying the binder composition to the fibers may be done by a variety of techniques including spraying, spin-curtain coating, curtain coating, and dipping-roll coating. The composition can be applied to freshly-formed fibers, or to fibers that have been cooled and processed (e.g., cut, coated, sized, etc.). The binder may be provided to the applicator as a premixed composition or may be supplied to the applicator in separate solutions for the crosslinking agent and the reducing sugar component. In some instances where the binder composition includes a solvent, a portion or all of the solvent may be removed from the composition before or after its application on the fibers.

The step of curing the binder composition may include exposing the composition applied to the fibers to an environment conducive to curing. For example, the curable amalgam of fibers and binder composition may be heated to a binder curing temperature. Exemplary binder curing temperatures may include a temperature range from 100° C. to 250° C. The curing amalgam may be heated to the curing temperature for a period of 1 minute to 100 minutes (e.g., 20 minutes).

The curing step may produce the finished fiber-containing composite, such as fiberglass insulation. In some exemplary methods, additional agents like an anti-dusting agent may be applied during or following the curing step.

Exemplary Binder Compositions

The present carbohydrate binder compositions may include one or more types of carbohydrate, nitrogen-containing compounds, and thickening agents, among other binder components. When the binder compositions are cured, the carbohydrates and nitrogen-containing compounds form a crosslinked polymer that in some instances is referred to as a Maillard polymerization product. Thickening agents are selected that create little or no interference with the crosslinking reaction of the polymer precursors so that the binder composition can be thoroughly and quickly cured after deposition on the fiber substrate (e.g., a glass fiber mat).

Exemplary thickening agents are added to control the viscosity of the binder compositions that are ultimately cured to make the adhesive binder component of the fiber product. The thickening agents may be polymeric materials and may be partially or fully water soluble. They are selected to enhance the binder compositions rheological properties (e.g., increase the composition's viscosity and surface tension) without substantially interfering with the composition's curability into an adhesive binder for the substrate fibers. Exemplary thickening agents may include polysaccharides, such as xanthan gum, guar gum, modified starches and the like; neutralized polyacrylic acid, such as sodium polyacrylate, modified celluloses, such as hydroxyethyl cellulose (HEC), carboxymethyl cellulose (CMC), as well as their soluble salts, polyacrylamides, and polyvinyl alcohols. The exemplary thickening agents may have a weight average molecular weight typically from 100,000 to 2,000,000 g/mol (e.g., 200,000 to 1,000,000 g/mol). The thickening agent (or agents) are typically added to the binder composition prior to its deposition on the fiber substrate, or alternatively may be added separately and approximately simultaneously with the other components of the binder composition to the fiber substrate.

The concentration of thickening agent in the binder composition may depend in part on the concentration of the other binder components in the composition. The carbohydrate binder compositions may be aqueous mixtures or solutions, and their viscosities depend in part on the how much the polymer precursors have been diluted by the water. For example, some concentrated binder compositions (e.g., solids concentrations of 45 to 70 wt. % or more) may have viscosities in the hundreds of centipoise at room temperature. The concentrated resins are typically diluted with water to, for example, a solids concentration of 10 to 30 wt. % solids (e.g., 10 to 20 wt. % solids), reducing the binder composition's viscosity to less than 3 cPs at room temperature. Other binder compositions may have functional viscosities at high concentrations (e.g., 20 cPs at 50 wt. % solids concentration) but should be diluted to address processing challenges such as LOI, weight, and uniformity problems for the applied binder composition.

Thickening agents may be added to increase the viscosity of the aqueous binder composition to a range of 7 to 50 cPs at room temperature (i.e., 20° C.), as measured by a Brookfield viscometer operating at a speed of 60 revolutions per minute. Typically, binder composition viscosities in this range can be achieved at thickening agent concentrations between 0.03 to 0.3 wt. % of the total composition. The concentration range of thickening agent can depend on the type of agent used. For example, adding hydroxyethyl cellulose to a concentration range of 0.05 to 0.3 wt. % may be sufficient to increase the composition's viscosity into a 7 to 50 cPs range. The same viscosity range may be met by adding 0.03 wt. % to 0.2 wt. % xanthan gum to the aqueous binder composition.

In addition to the thickening agents, the binder compositions may also contain a surfactant that provides more precise control over the surface tension of the composition. The surfactant may be added in amounts to achieve a surface tension for the binder composition of 35 to 50 mN/m (e.g., 38 to 48 mN/m, 40 to 47 mN/m, etc.). These surfactants may include cationic, anionic, and/or non-ionic surfactants.

The binder formulations of the binder compositions may include one or more types of carbohydrates and nitrogen-containing compounds. The nitrogen-containing compounds may act as crosslinking agents for the carbohydrates in the cured binder. The carbohydrates used in the binder formulations may include reducing sugars that contain at least one aldehyde or ketone group, or are capable of forming an aldehyde or ketone group through isomerization. Exemplary reducing sugars may include glucose (dextrose), fructose, glyceraldehyde, galactose, allose, xylose, ribose, maltose, cellobiose, and lactose, among others.

The nitrogen-containing compounds may include a variety of compounds that can distinguish the class of binder formulation. One class of binder formulations uses an amino-amide as the nitrogen containing compound, which itself is a reaction product of an amine with a saturated or unsaturated reactant. Another class of binder formulations has as the nitrogen-containing compound a reaction product of a urea compound and aldehyde-containing compound. Each of these classes of nitrogen-containing compounds are described more detail below.

1. Carbohydrate/Amino-Amide Binder Formulations

The nitrogen-containing compounds may include amines capable of undergoing conjugate addition with a saturated or unsaturated reactant to form an amino-amide. The amino-amide then reacts during curing with the carbohydrate to form a polyimide. The amino-amide addition products may be formed by mixing the amine and saturated or unsaturated reactant in an aqueous medium at room temperature. The resulting addition products are either water-soluble, water-dispersible, or are present as an emulsion. In some binder formulations, the formation of the amino-amide from the reaction of the amine precursor with the saturated or unsaturated reactant may occur before the introduction of the carbohydrate, while other formulations mix all three precursors (i.e., the amine, saturated or unsaturated reactant, and carbohydrate) before the amino-amide is formed.

Each amine may have two or more primary and/or secondary amine groups to react and crosslink two or more carbohydrate molecules. The amines may include aliphatic, cycloaliphatic and aromatic amines. They may be linear or branched, and have additional functionalities and linkages such as alcohols, thiols, esters, amides, acids, and ethers, among others. Exemplary amines may include 1,2-diethylamine, 1,3-propanediamine, 1,4-butanediamine, 1,5-pentanediamine, 1,6-hexanediamine, diaminoxylene, diethylenetriamine, triethylenetetramine, tetraethylenepentamine, as well as combinations of two or more of these amines. Natural and synthetic amino acids such as lysine, anginine, hestidine, etc., may also be used.

The curable amino-amide is formed through the selection of an unsaturated or saturated reactant that is an anhydride, carboxylic acid, ester, and salts and mixtures of such reactants. These unsaturated reactants may include maleic acid, fumaric acid, maleic anhydride, mono- and di-esters of maleic acid and fumaric acid, and salts and mixtures of these. Ammonium salts of the unsaturated acids of their monoesters conveniently can be utilized. Saturated reactants may include, without limitation, succinic anhydride, succinic acid, mono and diesters of succinic acid, glutaric acid and anhydride, phthalic acid and anhydride, tetrahydro phthaic acid and anhydride, mono and diesters of acid anhydrides and salts of the acids, and their mono esters.

In some formulations, the amino-amide product may be oligomerized before reacting with the carbohydrate. This oligomerization may be facilitated by heating the amino-amide solution until the amino-amide is dimerized, trimerized, tetramerized, etc., into the amino-amide oligomer. The heating conditions may include raising the temperature of the amino-amide solution to, for example, 120° C. to 150° C. for a time of up to 5 hours. In some instances, the oligomerized amino-amide product forms a stronger, more rigid cured binder product than then amino-amide monomer.

Then during the binder curing step, the majority of the carbohydrate reacts with the amino-amide intermediate, which contains an amic acid functional group, (i.e., an amide linkage in the vicinity of a carboxylic acid). An amic acid functional group is typically more reactive than a simple carboxylic acid. The amount of carbohydrate added is generally such that the molar ratio of carboxylic acid in the amino-amide to carbonyl or ketone in the carbohydrate is from 1:5 to 50:1, for example a ratio of 1:20 to 20:1, or a ratio of 1:10 to 10:1. Additional details about carbohydrate/amino-amide binder formulation are described in co-assigned U.S. patent application Ser. No. 12/539,263 to Shooshtari et al, filed Aug. 11, 2009, and titled "Curable Fiberglass Binder," the entire contents of which are herein incorporated by reference for all purposes.

2. Carbohydrate/Urea Derivative Binder Formulations

The nitrogen-containing compounds may include urea derivative reaction products of urea (i.e., $H_2N-CO-NH_2$), and/or substituted ureas, with diformaldehyde compounds such as glyoxal. One specific class of these urea derivatives include imidazolidine compounds such as 4,5-dihydroxy-imidazolidin-2-one, which has the chemical structure:

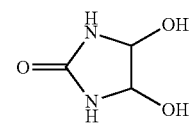

4,5-dihydroxyimidazolidin-2-one

More specifically, the urea compound may be a substituted or unsubstituted urea having the formula:

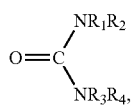

where $R_1$, $R_2$, $R_3$, and $R_4$ are independently chosen from a hydrogen moiety (H), an alkyl group, an aromatic group, an alcohol group, an aldehyde group, a ketone group, a carboxylic acid group, and an alkoxy group. Exemplary alkyl groups include straight-chained, branched, or cyclic hydrocarbons of varying size (e.g., $C_1$-$C_{12}$, $C_1$-$C_8$, $C_1$-$C_4$, etc.). Exemplary aromatic (i.e., aryl) groups include substituted or unsubstituted phenyl moieties, among other aromatic constituents. Exemplary alcohol groups include —ROH, where R may be a substituted or unsubstituted, saturated or unsaturated, branched or unbranched, cyclic or acyclic, organic moiety. For example, R may be —$(CH_2)_n$—, where n may be 1 to 12. Exemplary alcohols may also include polyols having two or more hydroxyl groups (—OH) in alcohol group. Exemplary aldehyde groups include —RC(=O)H, where R may be a monovalent functional group (e.g., a single bond), or a substituted or unsubstituted, saturated or unsaturated, branched or unbranched, cyclic or acyclic, organic moiety, such as —$(CH_2)_n$—, where n may be 1 to 12. Exemplary ketone groups may include —RC(=O)R' where R and R' can be variety of carbon containing constituents. Exemplary carboxylic acid groups may include —R—COOH, where R may be a monovalent functional group, such as a single bond, or a variety of carbon-containing constituents. Exemplary alkoxy groups include —$OR_x$, where $R_x$ is an alkyl group.

The aldehyde-containing compound may contain one or more aldehyde functional groups. Exemplary aldehyde-containing compounds include acetaldehyde, propanaldehyde, butyraldehyde, acrolein, furfural, glyoxal, gluteraldehyde, and polyfurfural among others. Exemplary aldehyde-containing compounds may also include substituted glyoxal compounds having the formula:

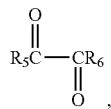

where $R_5$ and $R_6$ may be independently hydrogen (H), an alkyl group, an aromatic group, an alcohol group, an aldehyde group, a ketone group, a carboxylic acid group, and an alkoxy group, among other groups.

The reaction products of the urea compound and the aldehyde-containing compound may include an imidazolidine compound having the formula:

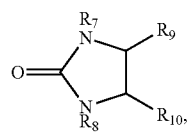

where $R_7$, $R_8$, $R_9$, and $R_{10}$ are independently, —H, —OH, —$NH_2$, an alkyl group, an aromatic group, an alcohol group, an aldehyde group, a ketone group, a carboxylic acid group, and an alkoxy group. In one specific example of the reaction between urea and glyoxal, the reaction product may be 4,5-dihydroxyimidazolidin-2-one.

The carbohydrate/urea derivative binder formulations may also include one or more catalysts to increase the rate of the crosslinking reactions between the carbohydrates and crosslinking agents when the composition is exposed to curing conditions. Exemplary catalysts may include alkaline catalysts and acidic catalysts. The acidic catalysts may include Lewis acids (including latent acids and metallic salts), as well as protic acids, among other types of acid catalysts. Lewis acid catalysts may include a salt of a deprotonized anion such as a sulfate, sulfite, nitrate, nitrite, phosphate, halide, or oxyhalide anion in combination with one or more metallic cations such as aluminum, zinc, iron, copper, magnesium, tin, zirconium, and titanium. Exemplary Lewis acid catalysts include aluminum sulfate, ferric sulfate, aluminum chloride, ferric chloride, aluminum phosphate, ferric phosphate, and sodium hypophosphite (SHP), among others. Exemplary latent acids include acid salts such as ammonium sulfate, ammonium hydrogen sulfate, mono and dibasic ammonium phosphate, ammonium chloride, and ammonium nitrate, among other latent acid catalysts. Exemplary metallic salts may include organo-titanates and organo-zirconates (such as those commercially manufactured under the tradename Tyzor® by DuPont), organo-tin, and organo-aluminum salts, among other types of metallic salts. Exemplary protic acids include sulfuric acid, phosphoric acid, hydrochloric acid, nitric acid, sulfonic acid compounds (i.e., R—S(=O)$_2$—OH) such as p-toluenesulfonic acid and methanesulfonic acid, and carboxylic acids, among other protic acids. Catalyst compositions may also include combinations of two or more catalysts, for example the combination of ammonium sulfate and diammonium phosphate.

The pH of the present binder compositions may vary depending upon the types and relative concentrations of the components used. Typically the pH of the present binder compositions are slightly acidic to alkaline with a pH range of about 6 to 8 (e.g., 6.5 to 7.5). The binder compositions have a pH that creates relatively little or no acid-based corrosion of metal fabrication equipment.

The reaction product of the urea derivative nitrogen-containing compound acts as a crosslinking agent for the carbohydrate. During a curing stage, the urea derivative can bond to two or more carbohydrates (either polymerized or unpolymerized) to form a crosslinked, polymeric cured binder.

The molar ratio of the (1) crosslinking reaction product of the urea compound and the aldehyde-containing compound to (2) the carbohydrate generally ranges from 1:2 to 1:50. Exemplary ratios of crosslinking agent to carbohydrate include a range from 1:4 to 1:10. Additional details about carbohydrate/urea derivative binder formulations are described in co-assigned U.S. patent application Ser. No. 13/490,638 to Shooshtari et al, filed Jun. 7, 2012, and titled "Formaldehyde-Free Binder Compositions with Urea-Formaldehyde Reaction Products," the entire contents of which are herein incorporated by reference for all purposes.

3. Carbohydrate/Nitrogen-Containing Salt Binder Formulations i. Salts of Inorganic Acids with Amines In additional carbohydrate binder formulations, the nitrogen-containing compounds may include a nitrogen-containing salt. For example, the nitrogen-containing compound may include the salt product of the combination of an inorganic acid and an amine (e.g., an amine-acid salt). Exemplary inorganic acids may include a phosphorous-containing acid such as phosphoric acid, pyrophosphoric acid, phosphorous acid, and phosphine, among others. Exemplary inorganic acids may also include oxygenated inorganic acids such as sulfuric acid, sulfurous acid, nitric acid, boric acid, hypochloric acid, chlorate acid, among others. They may also include non-oxygenated inorganic acids such as hydrochloric acid and hydrogen sulfide, among others.

Exemplary amines may include polyamines (e.g., diamines, triamines, etc.) having at least one primary amine group. For example, the amines may include ethylene diamine, 1,3-propanediamine, 1,4-butanediamine, 1,5-pentanediamine, 1,6-hexanediamine, a, a'-diaminoxylene, diethylenetriamine, triethylenetetramine, tetraethylenepentamine, as well as combinations of two or more of these amines.

When the amine-acid salt reacts with the carbohydrate under binder curing conditions the binder is formed. Exemplary binder systems include the combination of an amine-acid salt of 1,6-hexanediamine and phosphoric acid with the carbohydrate dextrose (HPD), the combination of an amine-acid salt formed from the combination of ethylene diamine and phosphoric acid with dextrose (EPD). Additional details about these amine-acid salt and carbohydrate binder formulations are described in co-assigned U.S. patent application Ser. No. 12/539,211, filed Aug. 11, 2009 to Shooshtari, the entire contents of which are herein incorporated by reference for all purposes.

ii. Salts of Inorganic Acids with Amines and Organic Species

Some carbohydrate/amine-acid salt binder formulations further include some combination of an organic acid, organic anhydride, and/or an alkanol amine. Exemplary organic acids may include polycarboxylic acid such as citric acid and or maleic acid. Exemplary organic anhydrides may include maleic anhydride, phthalic anhydride, methylphthalic anhydride, glutaric anhydride, tetrahydrophthalic anhydride, perhydrophthalic anhydride, itaconic anhydride, succinic anhydride, and trimellitic anhydride, among other anhydrides.

Exemplary alkanol amines may have the formula:

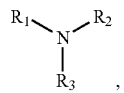

where $R_1$, $R_2$, and $R_3$ are independently chosen from, a hydrogen, a $C_{1-10}$ alkyl group, an aromatic group, and a $C_{1-10}$ hydroxy alkyl group, and wherein at least one of $R_1$, $R_2$, and $R_3$ is a hydroxyl alkyl group.

Specific examples of alkanol amines may include methanol amines such as mono-, di-, and tri-, methanol amine; ethanol amines such as monoethanol amine (MEA), diethanol amine (DEA), and triethanol amine (TEA); isopropanol amines such as mono-, di-, and tri-, isopropanol amine; methyldiethanol amine; ethyldiethanol amine; propyldiethanol amine; isopropyldiethanol amine; and n-butyldiethanol amine, among others.

Exemplary carbohydrate binder formulations may include the combination of a carbohydrate, amine-acid salt, and organic acid. These include binder formulations of dextrose, ethylene diamine phosphate, and citric or maleic acid. Additional details about these carbohydrate/amine-acid salt/ organic acid binder formulations are described in co-assigned U.S. patent application Ser. No. 13/478,765, filed May 23, 2012 to Shooshtari et al., the entire contents of which are herein incorporated by reference for all purposes.

Exemplary carbohydrate binder formulations may also include the combination of a carbohydrate, amine-acid salt, organic anhydride, and alkanol amine. This include binder formulations of the reaction products of monoethanol amine ("E") and maleic anhydride ("M") combined with ethylenediamine phosphate ("EP") and dextrose ("D") to make binder compositions referred to as EMEPDs. In still other exemplary binder formulations, the amine-acid salt may be eliminated. This includes formulations of the reaction products of monoethanol amine ("E") and maleic anhydride ("M") with the carbohydrate dextrose to make binder compositions referred to as EMDs. Additional details about these carbohydrate/amine-acid salt/anhydride-alkanol amine binder formulations are described in co-assigned U.S. patent application Ser. No. 13/559,769, filed Jul. 27, 2012 to Shooshtari et al., the entire contents of which are herein incorporated by reference for all purposes.

Exemplary binder formulations may include additional compounds combined with the reducing sugar, organic acid, and amine salt of an inorganic acid. For example, urea may also be included with the other binder components. Exemplary, urea-containing binder compositions may include ethylene diamine phosphate ("EP"), citric acid ("C"), urea ("U"), and dextrose ("D") combined to make a binder composition referred to as EPCUD. Exemplary molar ratios of these components may include Ethylenediamine:Phosphoric Acid:Citric Acid:Urea:Dextrose of 1:1:0.5:1:6.

iii. Ammonium Salts of Carboxylic Acids

In still additional carbohydrate binder formulations, the nitrogen-containing compounds may include an ammonium salt of a polycarboxylic acid. Exemplary ammonium salts of polycarboxylic acids may be formed from the reaction of ammonia ($NH_3$) with the polycarboxylic acid to form the ammonium salt. It should be appreciated that other types of ammonium ions can function as the cation in the ammonium-polycarboxylate salt, such as $(NH_3R_1)^+$, $(NH_2R_1R_2)^+$, and $(NHR_1R_2R_3)^+$, where $R_1$, $R_2$, and $R_3$ are each independently chosen from an alkyl, cycloalkyl, alkenyl, cycloalkenyl, hetrocyclyl, aryl, and heteroaryl, among other organic groups.

Exemplary polycarboxylic acids may include dicarboxylic acids, tricarboxylic acids, etc. Dicarboxylic acids may include maleic acid, and tricarboxylic acids may include citric acid.

The binder formulations may include the combination of a carbohydrate (e.g., a reducing sugar) with the ammonium salt of the polycarboxylic acid. For example, the binder composition may include dextrose and triammonium citrate.

4. Carbohydrate Blends with Latex and/or Solution Polymers

This group of carbohydrate binder compositions is distinguished by the inclusion of the components of a second binder in the formulation. The second binder may be a latex binder and/or solution polymer with a significantly higher viscosity than the carbohydrate binder composition. In some instances, the second binder may act as the sole thickening agent in the carbohydrate binder composition, while in other instances the second binder may complement other thickening agents to get the composition to a target viscosity.

The second binder may include latex binders having a Brookfield viscosity of about 100 cPs or more (spindle 18 operating at a speed of 60 rpm) at 20° C. Exemplary second binders may include acrylic binders, among others. The second binder may be present up to about half the weight of the total binder composition (e.g., 1 to 50 wt. %; 1 to 20 wt. %; etc.).

5. Additional Binder Components

The present carbohydrate binder compositions may further include one or more additional components such as adhesion prompters, oxygen scavengers, solvents, emulsifiers, pigments, organic and/or inorganic fillers, flame retardants, anti-migration aids, coalescent aids, curing catalysts, wetting agents, biocides, plasticizers, organosilanes, anti-foaming agents, colorants, waxes, suspending agents, anti-oxidants, and secondary crosslinkers, among other components. In some instances, some or all of the additional components are pre-mixed with the binder composition before it is applied to fibers and cured. In additional instances, some or all of the additional components may be introduced to the curable, curing, and/or cured fiber-containing composite during or after the initial binder composition is applied to the fibers.

Example 1

Binder compositions of dextrose and an amine salt of a phosphoric acid were prepared. Up to 0.5 mole of urea was added to a mole of the binder composition. The salt was made from one mole of 1,6-hexanediamine or ethylene diamine with one mole of phosphoric acid. A mole of the binder in this example is defined by the number of moles of diamine salt in the binder. Binder compositions with the different amounts of urea and citric acid were cured at temperatures of 180° C., 200° C., and 220° C. The level of the volatile organic compounds emitted during curing was evaluated with a gas chromatograph with an FID detector. Compositions with urea reduced the VOC emission by 50% over compositions without urea. No degradation in binder processing, mechanical performance, or humid aging of the binder was observed.

Example 2

Binder compositions of dextrose and an amino-amide were prepared. The amino-amide was the reaction product of phosphoric acid and 1,6-hexanediamine or ethylene diamine with one mole of maleic anhydride. One mole of urea and 0.5 mole of citric acid for each mole of binder were added to the binder composition. One mole of binder in this example is defined by the number of moles of amino-amide in the binder. Binder compositions with the different amounts of urea were cured at temperatures of 180° C., 200° C., and 220° C. The level of the volatile organic compounds emitted during curing was evaluated with a gas chromatograph. Compositions with urea reduced the VOC emission by 60% over compositions without urea. Smoke produced was reduced to zero opacity with binder compositions that included urea. No degradation in binder processing, mechanical performance, or humid aging of the binder was observed.

Example 3

Binder compositions of dextrose and dihydroxy ethyleneurea (DHEU) were prepared. To these compositions, various levels of urea were added. Levels of urea were varied from 0.1 mole to 1.0 mole based on the moles of the binder. In this example, the moles of the binder are determined by the moles of the DHEU. Urea at 0.1 mole per mole of DHEU was able to reduce VOCs by 40% and decrease smoke opacity by 70%.

Example 4

A plant trial on insulation batt with various densities and thicknesses was conducted. Products with R-values ranging from R-11 to R-40 using the binders of Example 1 and Example 3 were prepared. The addition of 0.1 mole of urea to the dextrose and diamine salt binder of Example 1 decreased oven smoke and opacity by 90%. The addition of 0.1 mole of urea to the dextrose and DHEU binder of Example 3 reduced oven smoke and opacity by 80%.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the salt" includes reference to one or more salts and equivalents thereof known to those skilled in the art, and so forth. The invention has now been described in detail for the purposes of clarity and understanding. However, it will be appreciated that certain changes and modifications may be practice within the scope of the appended claims.

What is claimed is:

1. A curable, carbohydrate binder composition comprising:
   a carbohydrate;
   a first urea compound; and
   a nitrogen-containing compound, wherein:
      the nitrogen-containing compound is not the first urea compound,
      the first urea compound is not the reaction product of a substituted or unsubstituted urea with a glyoxal, and
      the nitrogen-containing compound is selected from the group consisting of an amino-amic acid, an inorganic salt of a diamine or a polyamine, an ammonium salt of a carboxylic acid, or a reaction product of a second urea compound with a glyoxal.

2. The curable, carbohydrate binder composition of claim 1, wherein the composition is substantially free of formaldehyde.

3. The curable, carbohydrate binder composition of claim 1, wherein the composition when cured at a temperature from 100° C. to 300° C. emits fewer volatile organic compounds than the composition without the first urea compound.

4. The curable, carbohydrate binder composition of claim 1, wherein the composition when cured emits 50% or less of volatile organic compounds emitted when the composition without the first urea compound is cured.

5. The curable, carbohydrate binder composition of claim 1, wherein the composition when cured emits 10% or less of volatile organic compounds emitted when the composition without the first urea compound is cured.

6. The curable, carbohydrate binder composition of claim 1, further comprising a carboxylic acid.

7. The curable, carbohydrate binder composition of claim 1, further comprising citric acid.

8. The curable, carbohydrate binder composition of claim 7, wherein the citric acid is present in an amount of 0.5 mole per 1 mole of the first urea compound.

9. The curable, carbohydrate binder composition of claim 1, wherein the molar ratio of the first urea compound to the nitrogen-containing compound is 0.5 or greater.

10. The curable, carbohydrate binder composition of claim 9, wherein:
the carbohydrate is dextrose,
the nitrogen-containing compound is amine salt of a phosphoric acid, and
the amine of the amine salt comprises 1,6-hexanediamine or ethylene diamine.

11. The curable, carbohydrate binder composition of claim 1, wherein the nitrogen-containing compound comprises the reaction product of the second urea compound with an equimolar amount of the glyoxal.

12. The curable, carbohydrate binder composition of claim 1, wherein the nitrogen-containing compound is an amino-amic acid.

13. The curable, carbohydrate binder composition of claim 1, wherein the nitrogen-containing compound is an inorganic salt of a diamine or a polyamine.

14. The curable, carbohydrate binder composition of claim 1, wherein the mechanical strength of the cured binder composition is not less than the mechanical strength of the cured binder composition without the first urea compound.

15. The curable, carbohydrate binder composition of claim 1, wherein the composition when cured produces smoke with 70% or less opacity when the composition without the first urea compound is cured.

16. The curable, carbohydrate binder composition of claim 1, wherein the composition when cured produces smoke with 90% or less opacity when the composition without the first urea compound is cured.

17. The curable, carbohydrate binder composition of claim 1, wherein the first urea compound has a formula

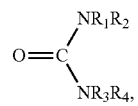

wherein $R_1$, $R_2$, $R_3$, and $R_4$ are independently chosen from a hydrogen moiety (H), an alkyl group, an aromatic group, an alcohol group, an aldehyde group, a ketone group, a carboxylic acid group, and an alkoxy group.

18. The curable, carbohydrate binder composition of claim 1, wherein:
the carbohydrate is dextrose,
the nitrogen-containing compound is dihydroxy ethyleneurea, and
the moles of the first urea compound to 1 mole of the nitrogen-containing compound is in a range from 0.1 mole to 1.0 mole.

19. A method of reducing volatile organic compound emission during curing of a binder composition, the method comprising:
forming an aqueous dispersion of fibers;
applying the binder composition to the aqueous dispersion of fibers to form a binder-fiber mixture; and
curing the binder-fiber mixture to form a fiber-containing composite, wherein:
the binder composition comprises a carbohydrate, a nitrogen-containing compound, and a first urea compound,
the nitrogen-containing compound is not the first urea compound,
the first urea compound is not the reaction product of a substituted or unsubstituted urea with a glyoxal, and
the nitrogen-containing compound is selected from the group consisting of an amino-amic acid, an inorganic salt of a diamine or a polyamine, an ammonium salt of a carboxylic acid, or a reaction product of a second urea compound with a glyoxal.

20. A fiber-containing composite comprising:
glass fibers;
a binder, wherein:
the binder comprises cured products from a binder composition comprising a carbohydrate, a first urea compound, and a nitrogen-containing compound that is not the first urea compound;
a reaction product of the first urea compound and an aldehyde or a ketone from a degradation product of the carbohydrate,
the first urea compound is not the reaction product of a substituted or unsubstituted urea with a glyoxal, and
the nitrogen-containing compound is selected from the group consisting of an amino-amic acid, an inorganic salt of a diamine or a polyamine, an ammonium salt of a carboxylic acid, or a reaction product of a second urea compound with a glyoxal.

* * * * *